United States Patent [19]
Walker et al.

[11] Patent Number: 5,207,667
[45] Date of Patent: May 4, 1993

[54] ONE HAND IV NEEDLE INJECTION SITE CONNECTOR

[75] Inventors: George T. Walker, San Diego; James M. Verespej, Carlsbad, both of Calif.

[73] Assignee: Block Medical, Inc., Carlsbad, Calif.

[21] Appl. No.: 768,374

[22] Filed: Sep. 27, 1991

[51] Int. Cl.$^5$ ............................................. A61M 25/00
[52] U.S. Cl. ................................. 604/905; 604/283
[58] Field of Search ........................... 604/200-206, 604/221, 239, 244, 283, 905, 411-414, 86, 88, 240, 243, 244, 403, 192

[56] References Cited

U.S. PATENT DOCUMENTS

| | | | |
|---|---|---|---|
| 4,439,193 | 3/1984 | Larkin | 604/905 |
| 4,752,292 | 6/1988 | Lopez et al. | 604/283 |
| 4,950,260 | 8/1990 | Bonaldo | 604/905 |
| 4,997,421 | 3/1991 | Palsrok et al. | 604/283 |
| 5,030,205 | 7/1991 | Holdaway et al. | 604/239 |
| 5,049,129 | 9/1991 | Zdeb et al. | 604/413 |

Primary Examiner—C. Fred Rosenbaum
Assistant Examiner—Manuel Mandez
Attorney, Agent, or Firm—Baker, Maxham, Jester & Meador

[57] ABSTRACT

A protected needle coupling for connecting to a conventional IV injection site comprises an elongated tubular housing having a proximal end and a distal end, a needle mounted at the proximal end and extending co-axially toward the distal end to a protected position within the housing, a connector at the proximal end for connecting to an IV tubing, and a telescoping tubular member reciprocally mounted in said housing and having axially extending slits defining a pair of opposed semi-cylindrical fingers extendable from the distal end of the housing, and having inwardly directed shoulders at the outer ends thereof for engaging a shoulder of an IV injection port for pulling the injection port into the housing for coupling engagement with the needle therein, and a tab extending outward from the telescoping member for manually forcing the telescoping member into the housing.

16 Claims, 1 Drawing Sheet

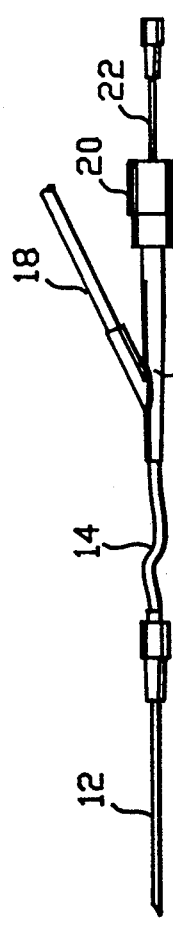
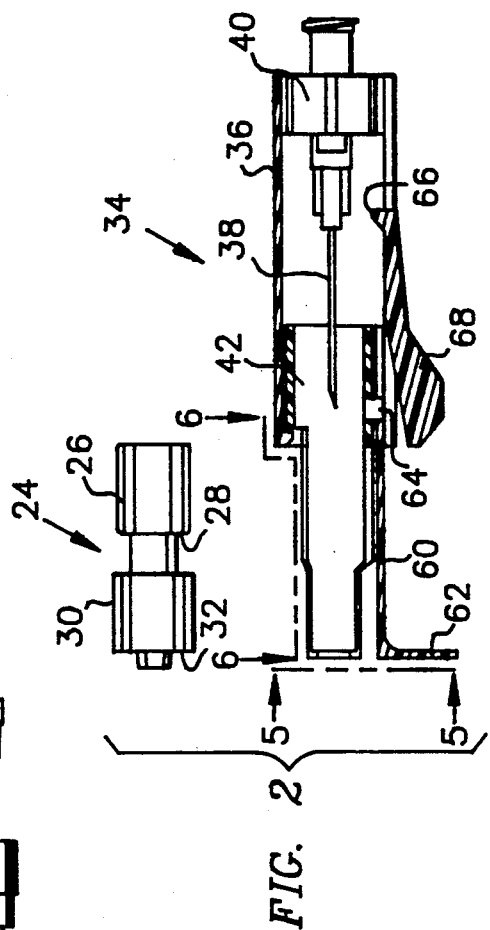
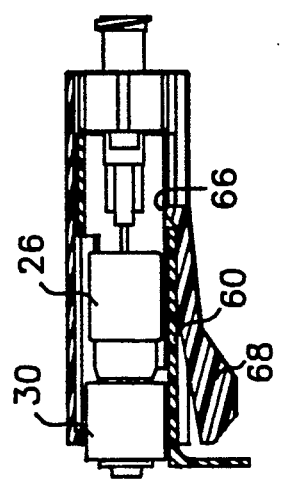
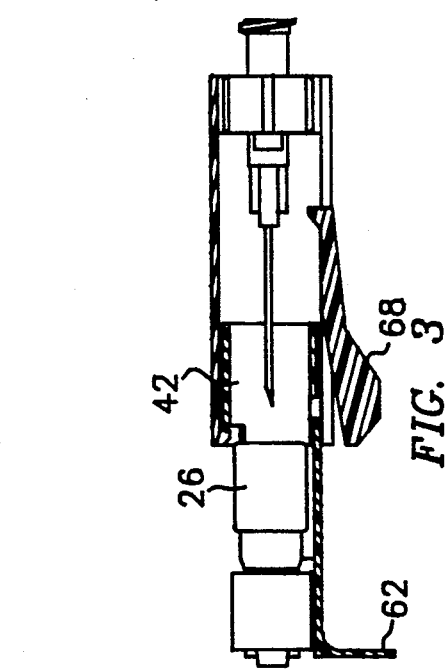
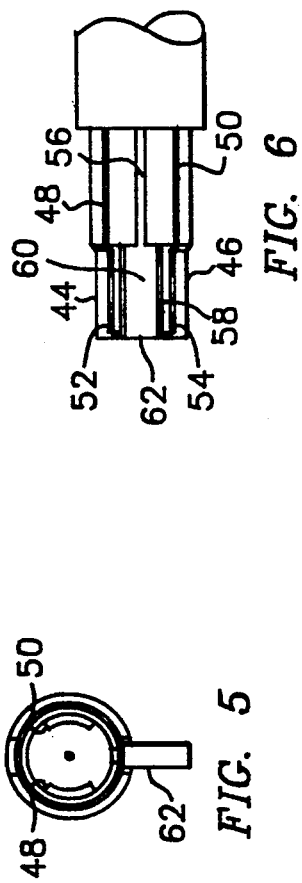
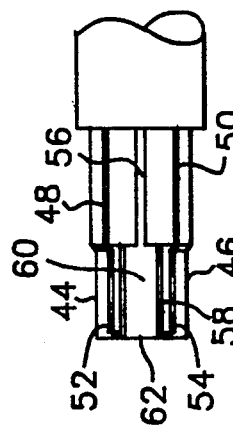

ONE HAND IV NEEDLE INJECTION SITE CONNECTOR

BACKGROUND OF THE INVENTION

The present invention relates to IV drug delivery apparatus and pertains particularly to an improved IV port or site needle coupling.

A great deal of medical therapy is carried out by way of intravenous (IV) injection of therapeutic solutions. Most treatments require multiple injections of at least one and frequently more solutions. In most instances, a patient is equipped with an injection site comprising a needle inserted into a vein, and equipped with a short length of tubing connected at one end to the needle, and having an injection port on the outer end thereof for insertion of a needle for connection to an IV fluid source.

The patient is connected to an IV source by means of a tubing set. An IV tubing set comprises a length of tubing having connectors on the ends and one or more injection sites or ports. The injection sites or ports enable the injection of additional medications or the like via a syringe or other IV source.

A portion of a typical or conventional IV tubing set is illustrated in FIG. 1. The overall IV tubing site, as illustrated, comprises a needle 12 for insertion into a patient connected to a tube 14 having a Y-site 16, and a tubing branch 18 for connection to a source of IV fluid (not shown). The Y-site includes a conventional IV injection site or port comprising an elastic plug and cap combination 20 of Neoprene or the like on or over the end of a portion of the Y-tube. The connection of an additional IV source for the injection of a fluid is accomplished by inserting a conventional needle 22 through the site or port 20 into the underlying tube.

The term "conventional" or "standard IV injection site or port", as used herein, comprises a tube end on which a combination elastomeric plug and cap is mounted. The plug portion inserts into the end of the tube, and the cap portion extends across the end and down the sides. Injection is accomplished by the insertion of a conventional needle connected to a syringe or other source through the hole in the plug and injecting the fluid. When the needle is removed, the hole in the plug or cap closes.

The conventional IV site or port has two major drawbacks. One major drawback is that it can be a source of contamination or infection. The coupling is typically exposed, as seen in FIG. 1, unless covered by means of a piece of surgical tape. Even the tape can be a source of contamination.

Another problem with the conventional IV site coupling is that the needle is uncovered prior to and as it is being moved into position for insertion into the elastic plug. This creates a hazard of accidental sticking or pricking the hand or fingers and injury and/or transmission of disease to the patient and/or the health care personnel.

Because of the high cost of administering health care in this country, many patients administer their own intravenous therapy (IV) at home. Many times, such therapy requires the periodic infusion of a fluid, such as an antibiotic and/or other medication. The patient is usually equipped with an IV catheter having one or more IV injection sites or ports for receiving an injection via a conventional needle coupling or connection.

The needle of the conventional syringe or IV coupling is a potential hazard, because it is normally unshielded.

Attempts have been made to overcome some of these problems by providing couplings that have a needle cover to protect the patient and health care person from being stuck by the needle. One example of such special couplings is available under the trademark Click Lock from ICU Medical, Inc. of Mission Viejo, Ca. These couplings, however, are of a special construction and cannot be used with the conventional or standard IV injection site or port. They require special coupling structures on the body of the IV injection site or port. These special couplings are expensive and not always readily available.

One solution to this problem is disclosed in co-pending U. S. application Ser. No. 07/659,751, entitled "Protected IV Needle Injection Site Coupling", by Gregory E. Sancoff, and assigned to Assignee hereof. However, that invention does not address other problems as discussed hereinafter.

Another major problem with these connectors is that they require two hands to connect. The patient is frequently alone when he needs therapy, and the tubing is normally mounted in one of the forearms and cannot be grasped with that hand. Thus, the patient cannot normally grasp the tubing or injection port on the tubing with one hand and insert the needle with the other.

It is desirable that a protective needle coupling exist that is useable with standard IV injection sites or ports and can be connected with one hand.

The present invention provides a needle protective coupling for conventional and non-standard IV injection sites or ports that can be connected by one hand.

SUMMARY AND OBJECTS OF THE INVENTION

It is the primary object of the present invention to provide an improved IV injection site protected needle coupling.

In accordance with a primary aspect of the present invention, an IV injection site coupling includes a protective needle coupling useable with a conventional IV injection site or port, and has means operative with one hand for grasping the injection port and pulling the connector and port into connecting engagement.

BRIEF DESCRIPTION OF THE DRAWING

The above and other objects and advantages of the present invention will become apparent from the following description when read in conjunction with the accompanying drawings wherein:

FIG. 1 is a plan view illustrating a prior art IV tubing set illustrating a conventional IV injection port or site and connection;

FIG. 2 is a side elevation view in section of a preferred embodiment of the invention in combination with a conventional IV injection port to be inserted therein;

FIG. 3 is a side elevation view like FIG. 2 showing the connector with the injection port positioned for connection;

FIG. 4 is a view like FIG. 2 showing the connector and port connected;

FIG. 5 is an end elevation view taken on line 5—5 of FIG. 2; and

FIG. 6 is a top plan view taken on line 6—6 of FIG. 2.

DETAILED DESCRIPTION OF PREFERRED EMBODIMENTS

Referring to the drawing, and particularly to FIG. 1, there is illustrated a typical IV tube set for connection of an infusion device to an IV site of a user. The illustrated tube set comprises an IV needle 12 for insertion into a vein of a patient's forearm or the like, with a catheter or tubing 14 connected thereto for connection to an IV source (not shown). The illustrated tubing set includes a Y-site 16 having a conventional injection site or port 20 thereon. A branch tube 18 connects to the IV source (not shown). A conventional needle 22 is inserted into the site or port to establish a conventional connection for IV injection from a second source (not shown).

An IV tubing set typically has one or more injection sites or ports for the injection of other IV fluids and the like. These additional fluids may typically be injected by a syringe or by an additional IV bag or infuser. The typical injection site connection utilizes a needle inserted into the cap of the injection site port. A conventional injection port comprises a short section of tubing, with an elastomeric cap or stopper made for example from Neoprene mounted over the end thereof. Referring to FIG. 1, the IV set includes an injection site or port 16, typically referred to as a Y-site. This is connected into the tubing between the IV solution source and the IV needle.

The injection site or port comprises a small section of tubing 18 having an end covered by a cap or stopper 20 of an elastomeric material, which can receive a needle and reseal the needle puncture when the needle is removed. The traditional connection or injection at an IV injection port utilizes a conventional needle 22, which is inserted through the cap 20 to communicate with the tubing 18, which in turn communicates with the IV tubing. This conventional connection is frequently wrapped with surgical tape overlapping the cap 20 and a portion of the needle to serve to retain the needle in place.

Referring to FIG. 2, an exemplary embodiment of the present invention is illustrated positioned for connection to an injection port 24. The illustrated conventional injection port 24 has a cap 26 of Neoprene or similar elastomeric material having a shoulder 28. A luer connector 30 for connection to tubing or the like also has a shoulder 32. The protected needle connection of the present invention, designated generally by the numeral 34, comprises a generally tubular housing 36 for protectively extending over and beyond the outer end of a conventional or standard needle 38 mounted in a suitable needle mount 40 mounted in one or a proximal end of the tubular housing.

The connector 34 of the present invention is constructed to be connected to an injection port of any design having a shoulder adjacent to or associated with the injection port. The exemplary embodiment illustrated is designed to particularly cooperate with convention injection ports of the type illustrated and designated generally at 24 for a one-hand connection thereto. The connector assembly as illustrated comprises telescoping guide means in a form of a tubular sleeve 42 reciprocally mounted within the tubular housing 36, and having a pair of opposed arms or fingers 44 and 46 for extending from the distal end of the housing for receiving an injection port moved laterally, as shown by the arrow between the fingers. The fingers are constructed for engaging an IV injection port for pulling the port into housing 36 for coupling engagement with a needle 38 therein, as will be subsequently explained.

The arms or fingers 44 and 46 are formed by longitudinally extending slits along a portion of the tubular sleeve 42, with one slit having a width, as shown in FIG. 6, for receiving the injection port inserted laterally therein. The fingers 44 and 46 are stepped down slightly in diameter at the outer ends thereof and are of a generally semi-cylindrical configuration, as can be seen in FIG. 5. The fingers 44 and 46 have inwardly extending shoulders 52 and 54 for engaging behind either shoulder 32 of the connector 30 or shoulder 28 of the port cap 26, as shown in FIGS. 3 and 4, for pulling the injection port into coupling engagement with the needle 38, as shown in FIG. 4.

The larger diameter portion of the fingers are formed at the bottom by a narrow slot 56 and at the outer end by a larger slot 58, as shown in FIG. 6. This gives the fingers a slight amount of flexibility so that they can yield for receipt of a injection port forced through the upper slot between slot edges 48 and 50 to be positioned between the fingers 44 and 46. Shoulders 52 and 54 engage a shoulder on the port to pull it into the housing.

The telescoping member is provided with a lower extension portion 60 and a tab 62 to enable the member and its extended fingers to be pressed back into the housing 34 and 36 by a thumb. The tubular member 42 is also provided with a recess or slot 64, engageable by a latch dog 66 of a latch lever 68 for releasably latching it in the innermost position, as shown in FIG. 4.

In operation, the user having a injection site with tubing attached to his arm selects a connector, as described above, and with the telescoping member 42 with fingers extending out of the end of housing 36 positions the fingers 44 and 46 with the open side or slot directly over the injection port assembly, (see FIG. 2) and presses the fingers down with shoulders 52 and 54 extended sufficiently back to engage behind shoulder 32. The fingers 44 and 46 are then forced down to encompass the injection port, and the thumb tab 62 is then engaged by the thumb and pressed to the right, as illustrated, forcing the telescoping guide member 42 into the housing 36 for biasing and guiding the injection port into engagement with the needle 38, as shown in FIG. 4. This establishes a connection between the one hand connector 34 and the injection port 24.

The telescoping member 42 is then latched into position, as shown in FIG. 4, by latch dog 66 engaging slot 64 and infusion can begin. Once infusion is completed, and it is desirable to disconnect the connector assembly, the above steps are simply reversed, with the latch lever 68 depressed to release the latch dog 66 from recess 64, permitting the thumb tab 62 to be engaged to push the telescoping assembly and injection port or head outward from needle 38 and housing 36 to the position as shown in FIG. 3. The connector then may be pulled sideways away from the open side of the fingers 44 and 46, permitting the injection port assembly 24 to be pulled out of the position between the fingers.

It will be appreciated that the connector may be utilized with any number of different injection ports so long as they have a shoulder that can be engaged by the outward extending opposing fingers 44 and 46. Thus, it enables a user to assemble and establish the connection with one hand.

While we have illustrated and described our invention by means of specific embodiments, it should be understood that numerous changes and modifications may be made therein without departing from the spirit and scope of the invention as defined in the appended claims. We further assert and sincerely believe that the above specification contains a written description of the invention and the manner and process of making and using it, in such full, clear, concise, and exact terms as to enable any person skilled in the art to which it pertains, or with which it is most nearly concerned, to make and use the same, and further that it sets forth the best mode contemplated by us for carrying out the invention.

We claim:

1. A protected IV injection site coupling for one hand connection to an IV injection port comprising:
   an elongated tubular housing having a proximal end and an open distal end;
   needle mounting means in said proximal end for mounting a conventional needle in a protected coaxial position within said housing and extending toward said distal end;
   connecting means at said proximal end for connection to an IV source; and
   telescoping means reciprocally mounted in said housing and having spaced apart opposed finger means extendable from said distal end of said housing for engaging an IV injection port therebetween for pulling said injection port into said housing upon movement of said telescoping means into said housing for coupling engagement with said needle therein.

2. A protected needle coupling according to claim 1 wherein said finger means have inwardly directed shoulder means at outer ends thereof for engaging a shoulder of an IV injection port.

3. A protected needle coupling according to claim 1 further comprising latching means for releasably latching said telescoping means in said housing.

4. A protected needle coupling according to claim 1 further comprising tab means extending outward from said telescoping means for manually forcing said telescoping means into said housing.

5. A protected needle coupling according to claim 1 wherein said telescoping means comprises a tubular sleeve and said finger means are formed by slits along said tubular sleeve.

6. A protected needle coupling according to claim 5 wherein one of said slits is wide enough to enable an injection port to extend laterally therein.

7. A protected needle coupling according to claim 4 wherein said finger means are substantially semi-cylindrical in configuration and have an opening at one side thereof for receiving said IV injection port, and shoulder means for engagement with an annular shoulder of said injection port.

8. A protected needle coupling according to claim 7 further comprising tab means extending outward from said telescoping means for manually forcing said telescoping means into said housing.

9. A protected needle coupling according to claim 8 further comprising latching means for releasably latching said telescoping means in said housing.

10. A detachable protected needle coupling for one hand detachable connection to an IV injection site comprising:
    an elongated tubular housing having a proximal end and a distal end;
    needle mounting means at said proximal end for mounting a conventional needle in a protected coaxial position within said housing for extending toward said distal end;
    connecting means at said proximal end for connection to an IV source; and
    telescoping tubular means mounted in said housing an having axially extending slits defining opposed finger means extendable from said distal end of said housing for engaging an IV injection port for pulling said injection port into said housing upon movement of said tubular means into said housing for coupling engagement with said needle therein.

11. A protected needle coupling according to claim 10 wherein said finger means have inwardly directed shoulder means at outer ends thereof for engaging a shoulder of an IV injection port.

12. A protected needle coupling according to claim 11 further comprising tab means extending outward from said telescoping means for manually forcing said telescoping means into said housing.

13. A protected needle coupling according to claim 12 further comprising latching means for releasably latching said telescoping means in said housing.

14. A protected needle coupling according to claim 13 wherein one of said slits is wide enough to enable an injection port to extend laterally therein.

15. A detachable protected needle coupling for one hand detachable connection to an IV injection port of IV infusion system comprising in combination:
    an elongated tubular housing having a proximal end and a distal end;
    a needle mounted at said proximal end and extending coaxial thereof toward said distal end with a tip disposed in a protected position within said housing;
    connecting means at said proximal end for connecting to an IV source
    telescoping tubular means reciprocally mounted in said housing for movement between innermost and outermost positions within said housing and having axially extending slits defining a pair of opposed semi-cylindrical fingers extendable from said distal end of said housing and having inwardly directed shoulder means at outer ends thereof for engaging a shoulder of an IV injection port for pulling said injection port into said housing upon movement of said tubular means away from said distal end to said innermost position for coupling engagement with said needle therein;
    tab means extending outward from said telescoping means for manually forcing said telescoping means between said innermost position and said outermost position in said housing; and
    latching means for releasably latching said telescoping means in an innermost position in said housing.

16. A protected needle coupling according to claim 15 wherein one of said slits is of sufficient width to enable an injection port to extend laterally therethrough for positioning between said fingers.

* * * * *